United States Patent
Bronstein et al.

[11] Patent Number: 5,336,596
[45] Date of Patent: Aug. 9, 1994

[54] MEMBRANE FOR CHEMILUMINESCENT BLOTTING APPLICATIONS

[75] Inventors: Irena Bronstein, Newton; Brooks Edwards, Cambridge; John Voyta, Sudbury, all of Mass.

[73] Assignee: Tropix, Inc., Bedford, Mass.

[21] Appl. No.: 811,620

[22] Filed: Dec. 23, 1991

[51] Int. Cl.$^5$ .................. C12B 1/68; G01N 33/545; B32B 27/00
[52] U.S. Cl. ........................ 435/6; 435/7.72; 435/7.92; 436/518; 436/528; 436/531; 252/700; 428/420; 428/475.8; 428/508
[58] Field of Search .............. 428/420, 475.8, 508; 422/52; 435/6, 7.72, 7.92, 96 L, 963, 968; 436/529, 530, 531, 518, 528; 252/700

[56] References Cited
U.S. PATENT DOCUMENTS

| | | | |
|---|---|---|---|
| 4,124,388 | 11/1978 | Bronstein-Bonte et al. | 96/29 D |
| 4,322,489 | 3/1982 | Land et al. | 430/213 |
| 4,340,522 | 7/1982 | Bronstein-Bonte et al. | 524/766 |
| 4,424,326 | 1/1984 | Land et al. | 526/265 |
| 4,503,138 | 3/1985 | Bronstein-Bonte et al. | 430/213 |
| 4,563,411 | 1/1986 | Bronstein-Bonte et al. | 430/213 |
| 4,794,090 | 12/1988 | Parham et al. | 436/531 |
| 4,978,614 | 12/1990 | Bronstein | 435/21 |

*Primary Examiner*—Esther L. Kepplinger
*Assistant Examiner*—Lora M. Green
*Attorney, Agent, or Firm*—Oblon, Spivak, McClelland, Maier & Neustadt

[57] ABSTRACT

A new and improved polymeric membrane for use in biological assays is provided. A blotting assay employing 1,2-dioxetanes as a source of chemiluminescence employs, as an improved membrane, a polymer comprised of at least one monomer of the formula:

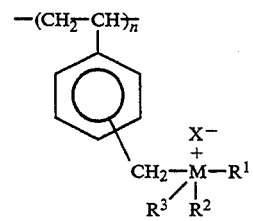

The membranes reduce background signal, improve sensitivity and reliability.

6 Claims, 6 Drawing Sheets

Nylon Membrane

Control      Polymer Coated    Polymer Coated
                               SDS Washed Polymer Coated
SDS Washed
NaCl Washed Control Nylon Membrane

MEMBRANE FOR CHEMILUMINESCENT BLOTTING APPLICATIONS

BACKGROUND OF THE INVENTION

1. Field of the Invention

This invention pertains to improved new membranes for use in connection with biological assays performed on membranes, specifically, chemiluminescent assays where the analyte is deposited on a membrane, and subjected to subsequent processing, the processing involving indicating the presence or absence and quantity of a suspected element in the analyte by the release of chemiluminescence. More specifically, this invention pertains to improved membranes which can be used in connection with chemiluminescent assays based on 1,2-dioxetanes which can be triggered by enzymes and enzyme conjugates in ligand-binding pairs to emit light.

2. Background of the Prior Art

Increasingly, blotting assays employing chemiluminescent detection have become a popular modality for the detection of proteins and nucleic acids. Conventionally, such assays are conducted by isolating a sample of the analyte on a membrane, exposing that membrane to an antibody-agent or nucleic acid probe agent complex, wherein the agent causes a composition to be added to undergo chemiluminescence. In its most widely practiced form, this type of blotting assay employs an enzyme or enzyme conjugate as the agent causing a compound which can decompose to release light to undergo that decomposition, thereby giving chemiluminescence. Among the most popular compounds for this purpose are 1,2-dioxetanes. These structures, if stabilized with an adamantyl group or similar stabilizing group, or derivatized adamantyl group, can be protected with an enzyme-labile group which, when cleaved by a suitable enzyme attached to the antibody or nucleic acid probe secured to the target compound of the analyte, forms an unstable anion, which then decomposes to release light. In this case, using an enzyme, the chemiluminescent compound is a substrate, and among dioxetane substrates, AMPPD disodium 3-(4-methoxy-spiro[1,2-dioxetane-3,2'-tricyclo[3.3.1.1.$^{3,7}$]decan]-4-yl) phenyl phosphate is widely used. Structurally related compounds, wherein the adamantyl group is substituted with various electron-active groups, convert the adamantyl moiety from a mere stabilizing agent to one which actively influences dioxetane decomposition. Among these, the chlorine-substituted compound, or CSPD, has been demonstrated to be markedly effective. A wide variety of other compounds, bearing other enzyme-labile protective groups, such as sugar, acetate and other ether and ester moieties are known and effective.

The protocol used in such blotting assays is conventional, and among various blotting assays, Western Southern Blotting are widely known. In such assays, proteins (or in related assays, nucleic acids) are purified, and transferred to membrane supports. Generally known membranes include nitrocellulose, nylon, PVDF and others. This transferred material (analyte) is incubated with at least one antibody specific for the compound being sought (specific protein or nucleic acid). In a Western Blotting assay the antibody can be complexed with an enzyme, or, a second antibody, complexed with an enzyme, can be added following a washing step. In the case of AMPPD and CSPD, the binder (antibody or DNA/RNA probe) is conjugated with an alkaline phosphatase enzyme. Subsequent to washing, the blot is incubated with the chemiluminescent substrate. Release of chemiluminescence is confirmation of the presence of the suspected compound or target analyte.

In Southern blotting procedures nucleic acid sample is blotted onto a membrane following gel electrophoresis separation. Hybridizations are performed with enzyme labeled nucleic acid probes (labiled directly or indirectly via biotin-avidin or antibody-antigen bridge) containing base sequence complementary to regions specific for the target sample. Again, subsequent to washing, the blot is incubated with the chemiluminescent substrate and the subsequent release of light signal is confirmation of the presence of the suspected nucleic acid sequence.

This blotting format presents certain problems in connection with the membrane supports identified. The chemical content of the membrane surface, to which the chemiluminescent substrate is exposed, has a tendency to quench or promote quenching of the emitted light, thus reducing the intensity of the chemiluminescent signal. Further, the membranes used have significant lot-to-lot variations, due to current production processes. As a result, it is difficult both to standardize the process, and to provide for automatic data acquisition. Among specific problems encountered are low signal levels, very high nonspecific backgrounds, and membrane-initiated decomposition of chemiluminescent substrates, such as AMPPD and CSPD.

When dealing with dioxetane substrates such as AMPPD, it is important to note that these compounds have very low intensities of chemiluminescence in aqueous, protic environments. This is believed to be due principally to proton transfer quenching reactions, or dipole-dipole interactions which tend to promote dark reactions of the excited state ultimately produced by enzyme cleavage. Proton transfer reactions are extremely well known in organic chemistry, and can easily compete with light emission during the lifetime of the excited state, which is several orders of magnitude slower. Shizuka, "Accounts of Chemical Research", 1985, Vol. 18, pages 141–147. This can be confirmed by the case that the chemiluminescent efficiency of AMPPD in aqueous buffers is approximately only $10^{-6}$, but improves, in the presence of a hydrophobic medium, by approximately $10^4$.

In addition to the above-noted problems, conventional blotting assays continue to leave certain goals unmet. Of particular importance is the ability to quantitate the levels of nucleic acid fragments, or proteins, identified in blotting applications. Currently, blotting assays are qualitative in nature, confirming only the presence or absence of the component sought for. Frequently, a component will be present in all analytes, but diagnosis of a disease depends on the level of the component in the analyte. Current blotting techniques do not permit discrimination on this basis.

Another unmet goal of blotting assays is the provision of membranes which will permit sharply resolved bands, corresponding to bound component, in the absence of background, which would be suitable for automated data acquisition. As an example, scanning charged-coupled devices can be employed in reading complex information such as DNA sequences. Such automation would permit higher efficiency of error-free data acquisition. Current blotting assays based on chemiluminescent compounds such as dioxetanes do not provide the necessary sharp resolution of bands or high intensity signal in the absence of background to permit automated data acquisition.

Accordingly, it remains a goal of those of skill in the art to obtain membranes which can be used for chemiluminescent blotting assays, based on enzyme-triggerable dioxetanes, to provide improved, quantifiable information.

SUMMARY OF THE INVENTION

The above goals are met, and other improvements more specifically described below are obtained, by providing a polymer coating for the membrane, the polymer itself comprising positively charged benzyl quaternary ammonium monomers. The polymer may be used to form the membrane itself, or may be used to coat any support, for use as a membrane. As the suitability for blotting assays of conventional membranes, such as nylon, PVDF and nitrocellulose are well known, these membranes, overcoated with the polymers of the claimed invention, are particularly suited. However, it should be stressed that virtually any inert support, overcoated with the polymer, can be used. In certain cases, the polymer itself can be cast on a surface, from which it is then released, for use as the membrane.

In a preferred embodiment, the coated membrane is washed with a SDS solution, followed by a saline and water wash. Even further improvements can be obtained by washing the membrane subjected to the SDS wash with 1 M NaCl in PBS, followed by a water wash. Substantial improvements in detection limits, reduction of background signal, and sharpness of band resolution are obtained, such that quantitation of the amounts of the component identified are possible. These membranes similarly provide substantial improvements in chemiluminescent DNA sequencing assays.

BRIEF DESCRIPTION OF THE DRAWINGS

FIGS. 1, 4 and 5 reflect nitrocellulose membrane based assays,

FIGS. 2 and 6 reflect nylon membrane based assays, and

FIG. 3 reflects an assay using a PVDF membrane. In each case, the "control" refers to an uncoated membrane of the identified type.

DETAILED DESCRIPTION OF THE INVENTION

Figure 1:
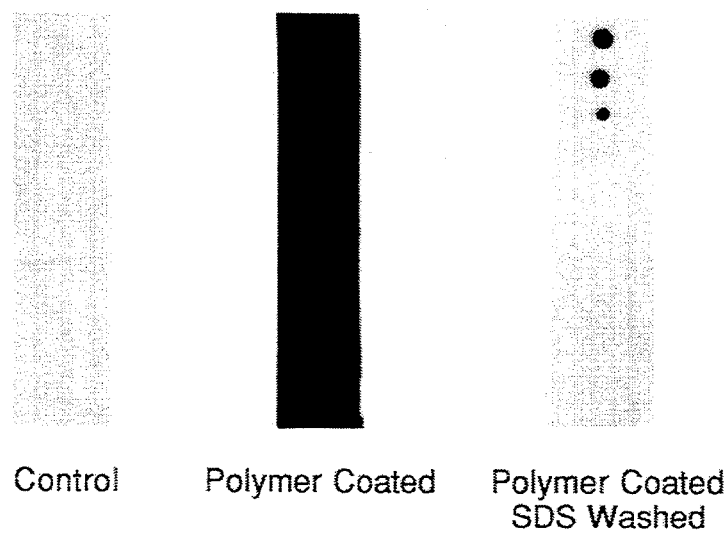
FIGS. 1-6 correspond to chemiluminescent results obtained through assays run employing the membranes of this invention.

The polymeric membranes, or membrane coatings of this invention, are based, in general, on polymeric onium salts, particularly quaternary salts based on phosphonium, sulfonium and, preferably, ammonium moieties. The polymers have the general formula I shown below:

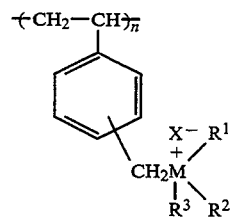

In this formula each of $R^1$, $R^2$ and $R^3$ can be a straight or branched chain unsubstituted alkyl group having from 1 to 20 carbon atoms, inclusive, e.g., methyl, ethyl, n-butyl, t-butyl, hexyl, or the like; a straight or branched chain alkyl group having from 1 to 20 carbon atoms, inclusive, substituted with one or more hydroxy, alkoxy, e.g., methoxy, ethoxy, benzyloxy or polyoxethylethoxy, aryloxy, e.g., phenoxy, amino or substituted amino, e.g., methylamino, amido, e.g., acetamido or ureido, e.g., phenyl ureido; or fluoroalkane or fluoroaryl, e.g., heptafluorobutyl, groups, an unsubstituted monocycloalkyl group having from 3 to 12 carbon ring carbon atoms, inclusive, e.g., cyclohexyl or cyclooctyl, a substituted monocycloalkyl group having from 3 to 12 ring carbon atoms, inclusive, substituted with one or more alkyl, alkoxy or fused benzo groups, e.g., methoxycyclohexyl or 1,2,3,4-tetrahydronaphthyl, a polycycloalkyl group having 2 or more fused rings, each having from 5 to 12 carbon atoms, inclusive, unsubstituted or substituted with one or more alkyl, alkoxy or aryl groups, e.g., 1-adamantyl or 3-phenyl-1-adamantyl, an aryl, alkaryl or aralkyl group having at least one ring and from 6 to 20 carbon atoms in toto, unsubstituted or substituted with one or more alkyl, aryl, fluorine or hydroxy groups, e.g., phenyl, naphthyl, pentafluorophenyl, ethylphenyl, benzyl, hydroxybenzyl, phenylbenzyl or dehydroabietyl; at least two of $R_1$, $R_2$ and $R_3$, together with the quaternary nitrogen atom to which they are bonded, can form a saturated or unsaturated, unsubstituted or substituted nitrogen-containing, nitrogen and oxygen-containing or nitrogen and sulfur-containing ring having from 3 to 5 carbon atoms, inclusive, and 1 to 3 heteroatoms, inclusive, and which may be benzoannulated, e.g., 1-pyridinium, 1-(3-alkyl or aralkyl)imidazolium, morpholino, alkyl morpholinium, alkylpiperidinium, N-acylpiperidinium, piperidino or acylpiperidino, benzoxazolium, benzthiazolium or benzamidazolium.

The symbol $X^-$ represents a counterion which can include, alone or in combination, moieties such as halide, i.e., fluoride, chloride, bromide or iodide, sulfate, alkylsulfonate, e.g., methylsulfonate, arylsulfonate, e.g., p-toluenesulfonate, substituted arylsulfonate, e.g., anilinonaphthylenesulfonate (various isomers), diphenylanthracenesulfonate, perchlorate, alkanoate, e.g., acetate, arylcarboxylate, e.g., fluorescein or fluorescein derivatives, benzoheterocyclic arylcarboxylate, e.g., 7-diethylamino-4-cyanocoumarin-3-carboxylate, organic dianionssuch as p-terephthalate may also be represented by $X^-$.

The symbol n represents a number such that the molecular weight of such poly(vinylbenzyl quaternary ammonium salts) will range from about 800 to about 200,000 (weight average), and preferably from about 20,000 to about 70,000, as determined by intrinsic viscosity or LALLS techniques.

Methods for the preparation of these polymers, related copolymers and the related starting materials where M is nitrogen are disclosed in G. D. Jones et al, *Journal of Polymer Science*, 25, 201, 1958; in U.S. Pat. Nos. 2,780,604; 3,178,396; 3,770,439; 4,308,335; 4,340,522; 4,424,326 and German Offenlegunsschrift 2,447,611.

The symbol M may also represent phosphorous or sulfur whereupon the corresponding sulfonium or phosphoniumpolymers have been described in the prior art: U.S. Pat. Nos. 3,236,820 and 3,065,272.

Methods of preparation of the two polymers of this invention are set forth in the referenced U.S. Patents, and do not constitute any aspect of this invention, per se.

Copolymers containing 2 or more different pendant oniumgroups may also be utilized in the invention described herein:

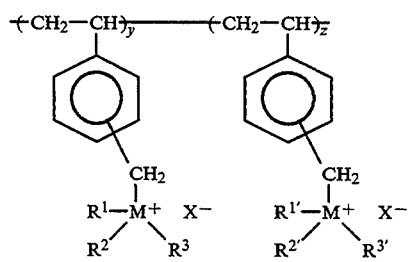

II

The symbols X, M', R$^{1'}$, R$^{2'}$, R$^{3'}$ are as described above for X, M, R$^1$–R$^3$. The symbols Y and Z represent the mole fraction of the individual monomers comprising the copolymer. The symbols Y and Z may thus individually vary from 0.01 to 0.99, with the sum always equalling one.

As preferred moieties, M is N, and R$^1$–R$^3$ are individually, independently, cycloalkyl, polycycloalkyl (e.g. adamantane) aralkyl or aryl, having 1 to 20 carbon atoms, unsubstituted or further substituted with hydroxyl, amino, amido, ureido groups, or combine to form via a spiro linkage to the M atom a heterocyclic (aromatic, aliphatic or mixed, optionally including other N, S or O hetero atoms) onium moiety.

X is preferably selected to improve solubility and to change ionic strength as desired, and is preferably halogen, a sulfate, a sulfonate. In copolymers, each of R$^1$–R$^3$ may be the same as or different from the corresponding R$^{1'}$–R$^{3'}$. Examples of preferred polymers include the following:

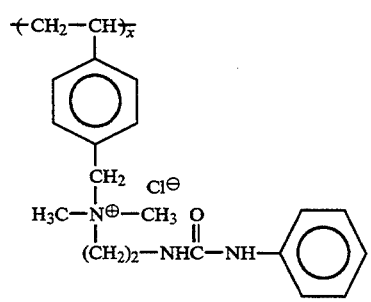

polyvinylbenzylphenylureidoethyldimethylammoniumchloride (PUDMQ)

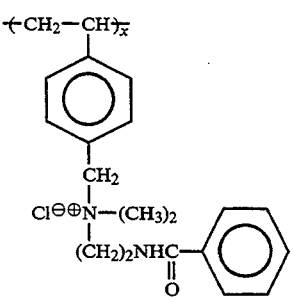

polyvinylbenzyldimethyl hydroxyethylammonium chloride (DMEQ)

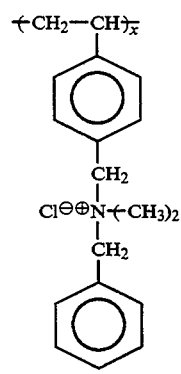

polyvinylbenzylbenzoylaminoethyldimethylammonium chloride (BAEDMQ)

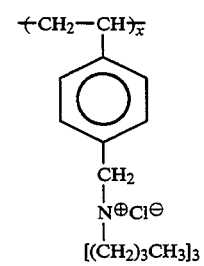

polyvinylbenzylbenzyldimethyl ammonium chloride (BDMQ)

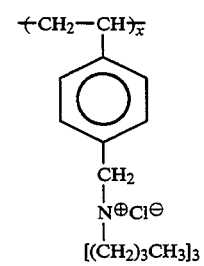

polyvinylbenzyltributyl ammonium chloride (TBQ)

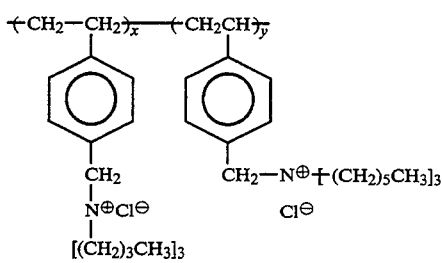

copolyvinylbenzyltrihexylammoniumchloride-polyvinylbenzyltributyl ammonium chloride (THQ-TBQ)

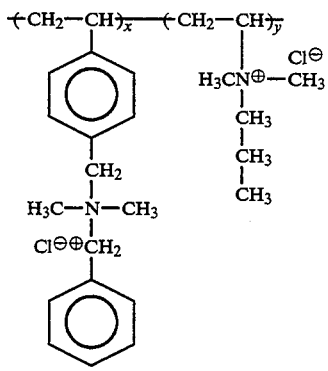

Copovinylbenzylbenzyldimethylammonium chloride-polyvinyl aminoethyldimethylammonium chloride (BDMQ-AEDMQ)

These vinylbenzyl quaternary ammonium salt polymers can be prepared by free radical polymerization of the appropriate precursor monomers or by exhaustive alkylation of the corresponding tertiary amines with polyvinylbenzyl chloride, or copolymers containing a pendant benzyl chloride function. This same approach can be taken using other polymeric alkylating agents such as chloromethylated polyphenylene oxide or polyepichlorohydrin. The same polymeric alkylating agents can be used as initiators of oxazoline ring-opening polymerization, which, after hydrolysis, yields polyethyleneimine graft copolymers. Such copolymers can then be quaternized, preferably with aralkyl groups, to give the final polymer.

Water soluble acetals of the polyvinylalcohol and a formylbenzyl quaternary ammonium salt, having the formula

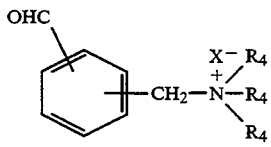

III wherein each $R_4$ is the same or a different aliphatic substituent and $X_1$ is an anion, as disclosed and claimed in Bronstein-Bonte et al U.S. Pat. No. 4,124,388, can also be used in practicing this invention. And, the individual vinylbenzyl quaternary ammonium salt monomers used to prepare the poly(vinylbenzyl quaternary ammonium salts) of formula I above can also be copolymerized with other ethylenically unsaturated monomers having no quaternary ammonium functionality, to give polymers such as those disclosed and claimed in Land et al U.S. Pat. No. 4,322,489; Bronstein-Bonte et al U.S. Pat. No. 4,340,522; Land et al U.S. Pat. No. 4,424,326; Bronstein-Bonte U.S. Pat. No. 4,503,138; Bronstein-Bonte U.S. Pat. No. 4,563,411; and Cohen et al U.S. Pat. No. 3,898,088, all of which polymers can also be used as enhancer substances in practicing this invention. Preferably these quaternized polymers will have molecular weights within the ranges given above for the poly(vinylbenzyl quaternary ammonium salts) of Formula I.

As it will be apparent to one skilled in the art, the use of cationic microgels or crosslinked latices are more suitable for the direct formation of cast membranes, but can also be used for the overcoating of preformed membranes. Such materials are well known as photographic mordants and may be synthesized using a monomer mixture which contains a crosslinking moiety substituted with two ethylenically unsaturated groups. Quaternary ammonium or phosphonium salt containing latices can be prepared using methodologies described in Campbell et al U.S. Pat. No. 3,958,995.

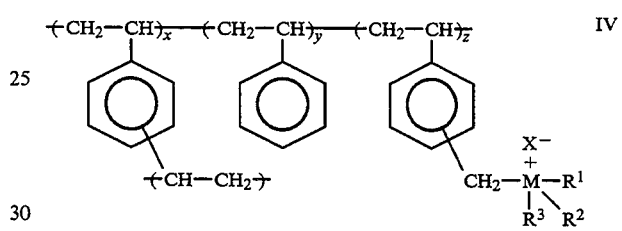

IV

Formula IV generally represents a useful subset of such water-soluble latex copolymers wherein the symbols $X^-$, $R^1$, $R^2$ and $R^3$ are as described above. The symbols X, Y and Z are mole fractions which must add together to give unity. The membrane is prepared by forming a thin coating over the polymer. If the polymer is to comprise the membrane, per se, the membrane is overcoated on a base support, such as glass, overcoated with a release solution. The monomeric solution can be prepared in deionized water, with ethanol to improve solubility or other conventional solvent. If cast by itself, the polisher is formed by drying at from 50–150° C. for a period of about 15 minutes.

As noted above, the polymer may be used as the membrane, alone, or as a coating on other supports, to lend stability to the poller. The only requirements the support must meet is that it be suitable for use in the physical manipulations of the assay, and be inert with respect to the elements of the assay. Glass plates, inert polymers, and the like, may be acceptable supports for overcoating with the polymer of the invention. Alternatively, these quaternary polymers and copolymers can be coated as a single layer from an admixture with nylon, PVDF, nitrocellulose and other polymeric binders. In one preferred embodiment, membranes already established as suitable for use in blotting assays, such as nylon membranes, PVDF and in particular nitrocellulose membranes, can function as the support, overcoated with the polymer of the invention. To overcoat a substrate, the polymer solution is deposited on the membrane strip, and rolled across the surface of the membrane, with, e.g., rubber tubing, to provide a uniform coating over the entire membrane. Alternative methods of coating, such as dipping, spraying and the like may be employed. The overcoated membrane is dried in an oven at 50–100° C. for about 15 minutes.

To improve resolution, and further reduce background signal, the polymer coatings of the membrane of the invention can be washed with sodium dodecyl sulfate (SDS). Typically, the membrane strips are washed with SDS, or other organic sulfonic salts and subsequently washed with water. Further improvements can be obtained with non-nylon membranes by SDS washing. Additional improvements can be obtained by following the SDS washing by a salt washing. Thus, the membrane strips, following the SDS washing, are washed with a sodium chloride solution, and again, washed with water.

EXAMPLES

This invention has been demonstrated in chemiluminescent assays for DNA as well as mouse IgG as representative of Western blotting for proteins. Each is discussed, in detail below. In each assay, seven different polymers A–G were employed. These polymers are selected from those set forth in the preferred examples above, as well as copolymers thereof. Specific formulations used were as follows:

A. PUDMQ/BDMQ 0.5/0.5
B. PUDMQ/BDMQ 0.3/0.7
C. DMEQ
D. BAEDMQ
E. TBQ
F. THQ-TBQ copolymer
G. BDMQ-AEDMA copolymer For both DNA and protein assays, each of nitrocellulose, PVDF and nylon membranes, currently commercially available, were coated with the polymer solutions of the strength indicated, according to the process described above. Specifically, coating solutions were prepared at 1.0%, 0.2% and in some cases, 0.02% and 0.002% strength, in deionized water containing 5% methanol. A puddle of coating solution was formed at one end of the membrane strip, and the solution was coated, uniformly, over the entire surface of the dry membrane by application of a piece of tygon rubber tubing, supported with a steel rod inside. The membranes were then subjected to detergent washing, followed by sodium chloride washing, as indicated below, and subsequently assayed. The results appear in Table 1 and Table 2, as the density of photographic images which were measured with a hand-held reflection densitometer (Tobias Association of Pennsylvania). The numbers in the column "background" and "signal at 210" are the actual reflection density units read off the densitometer. The column "Det.Lim." corresponds to the lowest amount of DNA detected, expressed in picograms.

Detergent Washing of Membranes

Pieces of each overcoated membrane were wetted with water and treated in a following fashion: first the membrane strips were incubated for 1 hour in 1% SDS at 65° C.; washed 4×10 minutes in 0.1% Tween-20 in phosphate buffered saline (PBS) at room temperature; washed 2×10 minutes in water, and subsequently air dried at room temperature. Control strips of non-overcoated membrane strips were also washed under the same conditions.

NaCl Washing of Membranes

Membrane strips which had been previously washed with SDS (as in Protocol 2) were further treated with NaCl in the following way: the dry membrane strips were wetted with 1% SDS in PBS and rinsed twice in water. Subsequently, the membranes were washed with 1M Na Cl in PBS for 1 hour at 65° C., and subsequently washed 2×10 minutes with 0.1% Tween-20 in PBS and 2×10 minutes with water, and air dried.

Chemiluminescent Evaluation of Coated Membranes

Serial dilutions of biotinylated pBR322-35 met were spotted onto all membrane strips. The final amount of spotted DNA was 210, 105, 52.5, 26.25, 13.13, 6.56, 3.28 and 1.64 picogram per spot. The DNA was subsequently fixed to the membrane strip by UV irradiation for 5 minutes. The membrane were then processed in the following fashion: first, they were wetted with 1×SSC, blocked with 0.2% casin, 0.1% Tween-20 in PBS for 30 minutes, incubated with 1–10,000 dilution of Avidx-alkaline phosphatase in 0.2% casein PBS. The membrane strips were subsequently washed 2×5 minutes in 0.2% casin, 0.1% Tween-20 in PBS; washed 2×5 minutes in 0.3% Tween-20, washed 2×5 minutes in substrate buffer (0.1 M diethanolamine, 1 mMMgCl$_2$, pH 10.0); incubated in 0.25 nlM AMPPD in substrate buffer, wrapped in plastic; and exposed to Kodak XAR x-ray film.

Detection of Proteins; Western Blotting

Mouse IgG was loaded on a gel in dilution of 20, 10, 5, 2.5, 1.25, 0.625, 0.313, 0.156, 0.078, and 0.039 nanograms per 10 μl, electrophoretically separated, then transferred to the following membrane strips:

A. SDS washed nitrocellulose
B. Unwashed nitrocellulose (no nitroblock)
C. Washed (SDS) HTQ-TBQ overcoated nitrocellulose
D. Washed (both SDS and NaCl) HTQ-TBQ overcoated nitrocellulose
E. Nitrocellulose with nitroblock
   1. Biodyne A (nylon)
   2. Biodyne A washed (SDS) HTQ-TBQ overcoated
   3. Biodyne A washed (both SDS and NaCl) HTQ-TBQ overcoated.

Subsequently, the membrane strips were blocked for 30 minutes in 0.2% casin, 0.1% Tween-20 in PBS, then incubated with anti-mouse IgG-alkaline phosphatase antibody (1–10,000 dilution) in PBS/0.1% Tween-20. The membrane strips were then washed 3×in PBS/0.1% Tween-20, and washed in the substrate buffer (0.1M diethanolamine, 1 mM MgCl$_2$, pH 10.0), and finally incubated in CSPD, and exposed to x-ray film.

TABLE 1

| Polymer | | Unwashed | | | Washed | | |
|---|---|---|---|---|---|---|---|
| | | Background | Signal at 210 pg | Det. Lim. | Background | Signal at 210 pg | Det. Lim. |
| Nitrocellulose, 5 minute exposure on x-ray film | | | | | | | |
| A | 1.0% | 0.03 | 0.03 | ns | 0.01 | 0.09 | 52.5 |
| | 0.2% | 0.01 | 0.01 | ns | 0 | 0.08 | 210 |

TABLE 1-continued

| | Polymer | Unwashed | | | Washed | | |
|---|---|---|---|---|---|---|---|
| | | Background | Signal at 210 pg | Det. Lim. | Background | Signal at 210 pg | Det. Lim. |
| B | 1.0% | 0.04–0.88 | 0.04 | ns | 0.01 | 0.58 | 105 |
| | 0.2% | 0 | 0 | ns | 0 | 0.05 | 210 |
| D | 1.0% | 0 | 0 | ns | 0 | 0.25 | 210 |
| | 0.2% | 0 | 0 | ns | 0 | 0 | ns |
| F | 1.0% | 1.0–1.3 | 1.1 | ns | 0 | 1.34 | 52.5 |
| | 0.2% | 0 | 1.2 | 105 | 0 | 1.31 | 105 |
| G | 1.0% | 0 | 0 | ns | 0 | 0.95 | 105 |
| | 0.2% | 0 | 0 | ns | 0 | 0.07 | 105 |
| | 0.02% | 0 | 0 | ns | 0 | 0 | ns |
| | 0.002% | 0 | 0 | ns | 0 | 0 | ns |
| control | 0% | 0 | 0 | ns | 0 | 0 | ns |
| Nylon, 5 minute exposure on x-ray film | | | | | | | |
| F | 1.0% | 1.32 | 1.32 | ns | 0.06 | 0.12 | 105 |
| | 0.2% | 0.06 | 1.32 | 13.1 | 0.03 | 0.05 | 105 |
| G | 1.0% | 1.0–1.31 | 1.0 | ns | 0.02 | 0.05 | 210 |
| | 0.2% | 0.03 | 0.06 | 210 | 0.02 | 0.03 | 210 |
| | 0.02% | 0.01 | 0.04 | 105 | 0.03 | 0.07 | 105 |
| | 0.002% | 0.02 | 0.16 | 26.3 | 0.02 | 0.41 | 26.3 |
| control | 0% | 0.01 | 0.08 | 210 | 0.01 | 0.03 | 210 |
| PVDF, 5 minute exposure on x-ray film | | | | | | | |
| G | 1.0% | 0.04 | 1.26 | 26.3 | 0.03 | 1.27 | 3.28 |
| | 0.2% | 0 | 0.19 | 52.5 | 0 | 0.23 | 52.5 |
| | 0.02% | 0 | 0.36 | 105 | 0 | 0.03 | 105 |
| | 0.002% | 0 | 0.31 | 52.5 | 0 | 0.03 | 210 |
| control | 0% | 0 | 0.07 | 105 | 0 | 0 | ns | ns = no detectable signal, or, no detectable signal above background

TABLE 2

| | Polymer | Unwashed | | | Washed | | |
|---|---|---|---|---|---|---|---|
| | | Background | Signal at 210 pg | Det. Lim. | Background | Signal at 210 pg | Det. Lim. |
| Nitrocellulose, 10 minute exposure on x-ray film | | | | | | | |
| A | 1% | HB | HB | ns | 0–0.07 | 1.27 | 6.5 |
| | 0.2% | 0 | 0 | ns | 0 | 0 | ns |
| | 0.02% | 0 | 0 | ns | 0 | 0 | ns |
| | 0.002% | 0 | 0 | ns | 0 | 0 | ns |
| B | 1% | HB | HB | ns | 0.02 | 1.37 | 1.55 |
| | 0.2% | 0 | 0 | ns | 0 | 0.13 | 105 |
| | 0.02% | 0 | 0 | ns | 0 | 0 | ns |
| | 0.002% | 0 | 0 | ns | 0 | 0 | ns |
| C | 1% | 0.05–0.17 | 0.17 | ns | 0 | 0 | ns |
| | 0.2% | 0 | 0 | ns | 0 | 0 | ns |
| | 0.02% | 0 | 0 | ns | 0 | 0 | ns |
| | 0.002% | 0 | 0 | ns | 0 | 0 | ns |
| D | 1% | 0.65–1.3 | ns | ns | 0 | 0.72 | 3.3 |
| | 0.2% | 0 | 0 | ns | 0 | 0.37 | 52.5 |
| | 0.02% | 0 | 0 | ns | 0 | 0 | ns |
| | 0.002% | 0 | 0 | ns | 0 | 0 | ns |
| E | 0.2% | 0.03 | 0.38 | 6.5 | 0 | 0.76 | 3.3 |
| | 0.02% | 0 | 0.05 | 210 | 0 | 0 | ns |
| | 0.002% | 0 | 0 | ns | 0 | 0 | ns |
| F | 1% | HB | HB | ns | 0.3 | 1.34 | 1.55 |
| | 0.2% | 0.1 | 1.36 | 1.55 | 0 | 1.34 | 1.55 |
| | 0.02% | 0 | 0.11 | 52.5 | 0 | 0 | ns |
| | 0.002% | 0 | 0 | ns | 0 | 0 | ns |
| Control | 0 | 0 | 0 | ns | 0 | 0 | ns |
| Nylon, 10 minute exposure on x-ray film | | | | | | | |
| A | 1% | 1.42 | 1.42 | ns | 1.41 | 1.41 | |
| | 0.2% | 0.23 | 1.06 | 105 | 0.14 | 1.3 | 52.5 |
| | 0.02% | 0 | 0.8 | 52.5 | 0 | 0.27 | 26.3 |
| | 0.002% | 0 | 1.06 | 13.1 | 0 | 0.27 | 13.1 |
| B | 1% | 1.4 | 1.4 | ns | 0.01 | 1.1 | 6.5 |
| | 0.2% | 0.07 | 0.31 | 105 | 0 | 0.07 | 26.25 |
| | 0.02% | 0.01 | 0.44 | 26.3 | 0 | 0.76 | 13.1 |
| | 0.002% | 0.01 | 0.62 | 52.5 | 0 | 0.06 | 52.5 |
| C | 1% | 0.94–1.4 | 1.4 | ns | 0 | 1.34 | 3.3 |
| | 0.2% | 0.03 | 0.43 | 52.5 | 0.01 | 1.12 | 6.5 |
| | 0.02% | 0.02 | 0.54 | 26.3 | 0 | 1.37 | 6.5 |
| | 0.002% | 0.02 | 0.47 | 26.3 | 0 | 1.42 | 6.5 |
| D | 1% | 1.4 | 1.4 | ns | 0.01 | 1.2 | 13.1 |
| | 0.2% | 0.03 | 0.2 | 105 | 0.01 | 0.23 | 26.3 |
| | 0.02% | 0 | 0.31 | 52.5 | 0 | 0.06 | 52.5 |

TABLE 2-continued

| | Polymer | Unwashed | | | Washed | | |
|---|---|---|---|---|---|---|---|
| | | Background | Signal at 210 pg | Det. Lim. | Background | Signal at 210 pg | Det. Lim. |
| | 0.002% | 0 | 0.45 | 52.5 | 0 | 0.1 | 52.5 |
| E | 0.2% | 0.14–0.2 | 1 | 105 | 0 | 1.11 | 3.3 |
| | 0.02% | 0.02 | 0.89 | 26.3 | 0 | 0.4 | 26.3 |
| | 0.002% | 0.02 | 0.46 | 26.3 | 0 | 0.2 | 26.3 |
| F | 0.2% | 0.11–0.5 | 1.36 | 52.5 | 0 | 1.37 | 1.55 |
| | 0.02% | 0.01 | 1.4 | 6.5 | 0 | 0.85 | 13.1 |
| | 0.002% | 0 | 1.3 | 6.5 | 0 | 0.79 | 13.1 |
| Control | 0 | 0.09 | 0.64 | 13.1 | 0 | 0.02 | 210 | ns = no detectable signal, or, no detectable signal above background

Figure 2:
Figure 2:
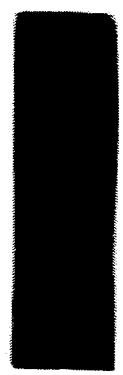
Figure 2:
Figure 3:
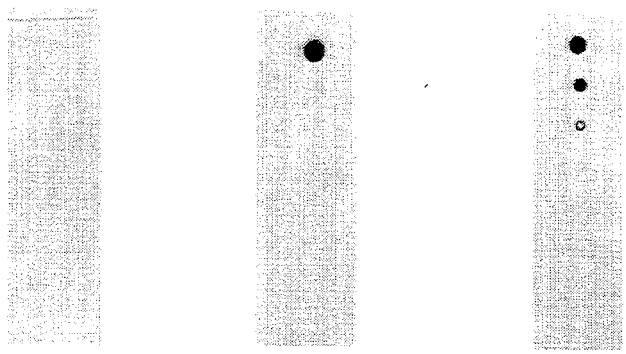
Figure 4:
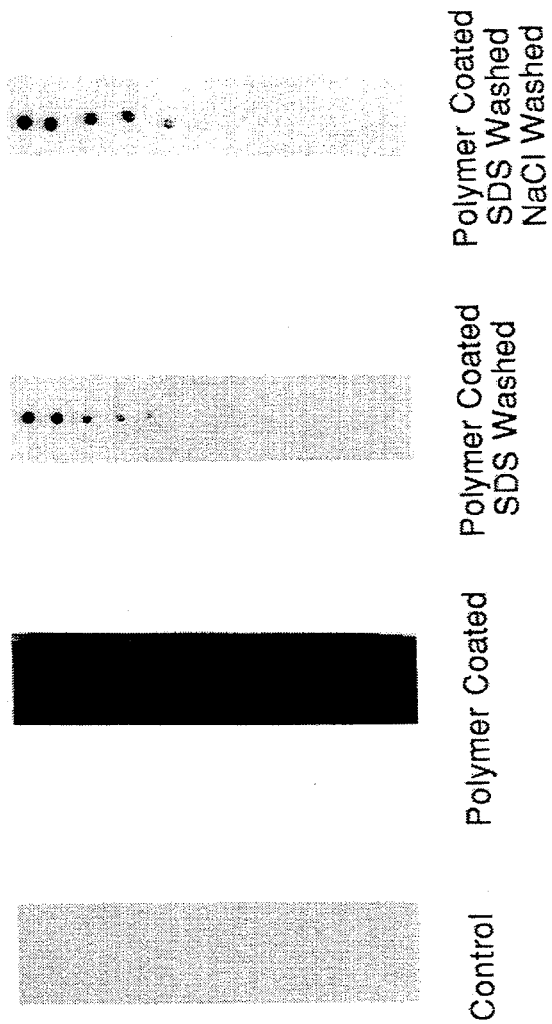
Figure 5:
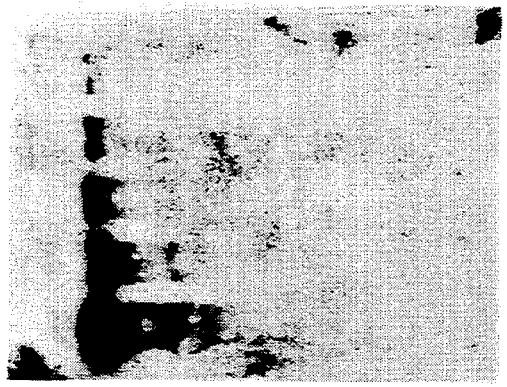
Figure 5:
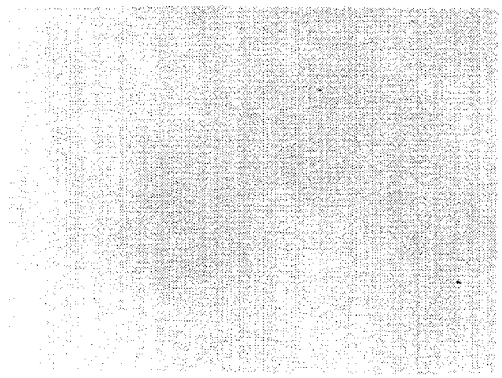
Figure 6:
Figure 6:
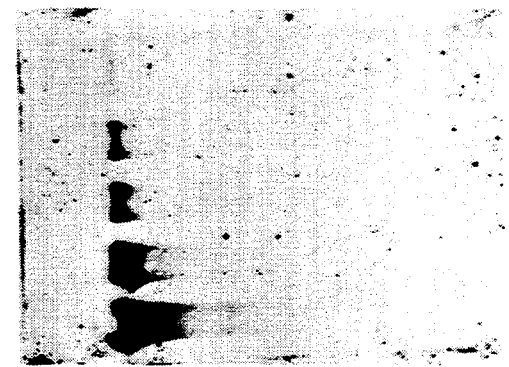

The assay results described above are illustrated in FIGS. 1–6. Each of these Figures compares a conventional membrane (control) and a coated membrane of the invention as indicated below.

| Figure | Membrane | Incubation Time (minutes) | Exposure Time (minutes) |
|---|---|---|---|
| 1 | Nitrocellulose | 10 | 10 |
| 2 | Nylon | 5 | 5 |
| 3 | PVDF | 5 | 5 |
| 4 | Nitrocellulose | 5 | 5 |
| 5 | Nitrocellulose | 10 | 5 |
| 6 | Nylon | 10 | 5 |

The invention has been described above with reference to generic formulation and specific example. The Examples are not limiting unless so indicated, and variations will occur to those of ordinary skill in the art. Among the variations, specific polymer formulations, coating strengths, membrane supports, chemiluminescent dioxetanes and the like will occur to those of skill in the art without the exercise of inventive faculty, and remain within the scope of the invention, save for the limitations of the claims recited below.

What is claimed is:

1. A membrane suitable for use in a blotting assay, comprising a support bearing a polymer coating, said support selected from the group consisting of nitrocellulose, nylon and PVDF, said polymer coating being selected from the group consisting of polyvinyl benzyl dimethyl hydroxyethyl ammonium chloride, polyvinyl benzyl benzoyl aminoethyl dimethyl ammonium chloride, polyvinyl benzyl tributyl ammonium chloride, copolymers of polyvinyl benzyl trihexyl ammonium chloride and polyvinyl benzyl tributyl ammonium chloride, copolymers of polyvinyl benzyl dimethyl ammonium chloride and polyvinyl aminoethyl dimethyl ammonium chloride and copolymers of polyvinyl benzyl phenyl ureidoethyl dimethyl ammonium chloride and polyvinyl benzyl dimethyl ammonium chloride, the molecular weight of said polymer being from 800–200,000, wherein said membrane is washed with a solution of sodium dodecyl sulfate.

2. The membrane of claim 1, wherein said washed membrane is further washed with a solution of sodium chloride.

3. A method of conducting a blotting assay wherein the presence of absence of a component of an analyte is determined, comprising the steps of:
   fixing said analyte on a membrane of claim 1,
   exposing said analyte on said membrane to a complex selected from an antibody enzyme complex and a nucleic acid probe-enzyme complex,
   allowing said antibody or nucleic acid probe to bind to any of said component present in said analyte,
   incubating the enzyme complex treated analyte with an enzyme-cleavable 1,2-dioxetane to cleave an enzyme-labile protecting group from said dioxetane thereby causing said dioxetane to decompose and chemiluminesce, and
   measuring the degree of chemiluminescence obtained, wherein the amount and presence of chemiluminescence indicates detection of said component.

4. The method of claim 3, wherein said 1,2-dioxetane substrate is AMPPD or CSPD.

5. A kit for conducting chemiluminescent blotting assays to determine the presence or absence of a component of an analyte, comprising:
   a) a dioxetane substrate bearing an enzyme-cleavable group which, when cleaved, causes said dioxetane to undergo decomposition and chemiluminesce,
   b) a complex selected from the group consisting of an antibody-enzyme complex and a nucleic acid probe-enzyme complex, said antibody or nucleic acid probe being specific for said component and said enzyme cleaving said enzyme-labile protecting group and
   c) a membrane of claim 1.

6. The kit of claim 5, wherein said dioxetane substrate is AMPPD or CSPD.

* * * * *

UNITED STATES PATENT AND TRADEMARK OFFICE
CERTIFICATE OF CORRECTION

PATENT NO. : 5,336,596

DATED : AUGUST 9, 1994

INVENTOR(S) : BRONSTEIN ET AL.

It is certified that error appears in the above-indentified patent and that said Letters Patent is hereby corrected as shown below:

Column 1, line 43, "[3.3.1.1.$^{3,7}$]" should read, --3.3.1.1$^{3,7}$]--.

lines 56-57 "Western Southern blotting" should read, --Western and Southern blotting--.

Column 2, line 9, "labiled" should read, --labeled--.

Column 4, line 61, "dianionssuch" should read, --dianions such--.

Column 6, lines 5-12, structure "Cl$^\ominus$——$^\oplus$N——(CH$_3$)$_2$" should read --Cl$^\ominus$ $^\oplus$N——(CH$_3$)$_2$--;

line 15, "hydroxyethylanunonium" should read --hydroxyethylammonium--.

UNITED STATES PATENT AND TRADEMARK OFFICE
CERTIFICATE OF CORRECTION

PATENT NO. : 5,336,596
DATED : AUGUST 9, 1994
INVENTOR(S) : BRONSTEIN ET AL.

It is certified that error appears in the above-indentified patent and that said Letters Patent is hereby corrected as shown below:

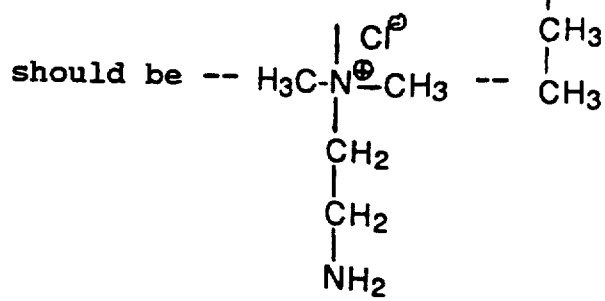

Column 7, line 32, "Copovinylbenzylbenzyldimethylammonium" should read, --Copolvinylbenzylbenzyldimethylammonium--.

UNITED STATES PATENT AND TRADEMARK OFFICE
CERTIFICATE OF CORRECTION

PATENT NO. : 5,336,596
DATED : AUGUST 9, 1994
INVENTOR(S) : BRONSTEIN ET AL.

It is certified that error appears in the above-indentified patent and that said Letters Patent is hereby corrected as shown below:

Column 8, line 40, "monomeric" should read --polymer--;
        line 43, "polisher" should read --polymer--;
        line 47, "poller" should read --polymer--.

Column 9, lines 48-49, "signal at 210" should read --signal at 210 pg--.

Column 10, line 16, "pBR322-35 met" should read --pBR322-35 mer--;
        lines 23, 27 and 52 "casin" should read --casein--;
        line 41, 43, 47 and 49 "HTQ-TBQ" should read --THQ-TBQ--;

Signed and Sealed this

Second Day of May, 1995

Attest:

BRUCE LEHMAN

Attesting Officer

Commissioner of Patents and Trademarks